United States Patent
Edwin et al.

(10) Patent No.: US 9,913,708 B2
(45) Date of Patent: *Mar. 13, 2018

(54) SELECTIVE ADHERENCE OF STENT-GRAFT COVERINGS

(71) Applicant: Bard Peripheral Vascular, Inc., Tempe, AZ (US)

(72) Inventors: Tarun J. Edwin, Chandler, AZ (US); Scott L. Randall, Mesa, AZ (US); Brendan McCrea, Ballwin, MO (US); Christopher E. Banas, Breckenridge, CO (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/348,180

(22) Filed: Nov. 10, 2016

(65) Prior Publication Data
US 2017/0056155 A1    Mar. 2, 2017

Related U.S. Application Data

(60) Division of application No. 14/310,527, filed on Jun. 20, 2014, now Pat. No. 9,492,269, which is a continuation of application No. 13/225,028, filed on Sep. 2, 2011, now Pat. No. 8,790,241, which is a continuation of application No. 11/363,689, filed on
(Continued)

(51) Int. Cl.
| | |
|---|---|
| *A61F 2/07* | (2013.01) |
| *A61F 2/90* | (2013.01) |
| *B29C 65/02* | (2006.01) |
| *B29C 65/48* | (2006.01) |

(Continued)

(52) U.S. Cl.
CPC .............. *A61F 2/07* (2013.01); *A61F 2/90* (2013.01); *B29C 65/02* (2013.01); *B29C 65/48* (2013.01); *A61F 2/91* (2013.01); *A61F 2002/072* (2013.01); *A61F 2002/075* (2013.01); *A61F 2230/005* (2013.01); *A61F 2230/0054* (2013.01); *A61F 2240/001* (2013.01); *A61F 2250/0003* (2013.01); *A61F 2250/0014* (2013.01); *A61F 2250/0039* (2013.01); *A61F 2250/0067* (2013.01); *B29L 2031/753* (2013.01)

(58) Field of Classification Search
CPC .... A61F 2/06; A61F 2/062; A61F 2/07; A61F 2/90; A61F 2002/072
See application file for complete search history.

(56) References Cited

U.S. PATENT DOCUMENTS 5,843,166 A * 12/1998 Lentz .................. A61F 2/07
                                                 623/1.13
6,139,573 A * 10/2000 Sogard ................ A61F 2/07
                                                 623/1.13

* cited by examiner

*Primary Examiner* — Charles A Marmor, II
*Assistant Examiner* — Carrie R Dorna
(74) *Attorney, Agent, or Firm* — C.R. Bard Intellectual Property Buchalter

(57) ABSTRACT

An endoluminal prosthesis including a radially expandable support member having interior and exterior surfaces and a wall with openings, a first covering member including a biocompatible polymer material at least partially positioned against the interior surface, and a second covering member including a biocompatible polymer material at least partially positioned against the exterior surface. The first covering member attaches to the second covering member at predetermined bonding locations within less than all of the openings thereby leaving unbonded regions.

6 Claims, 7 Drawing Sheets

Related U.S. Application Data

Feb. 27, 2006, now Pat. No. 8,012,194, which is a continuation of application No. 10/410,589, filed on Apr. 9, 2003, now Pat. No. 7,004,966, which is a continuation of application No. 09/764,811, filed on Jan. 16, 2001, now Pat. No. 6,547,814, which is a continuation of application No. 09/409,209, filed on Sep. 30, 1999, now Pat. No. 6,245,099.

(60) Provisional application No. 60/102,518, filed on Sep. 30, 1998.

(51) Int. Cl.
*A61F 2/91* (2013.01)
*B29L 31/00* (2006.01)

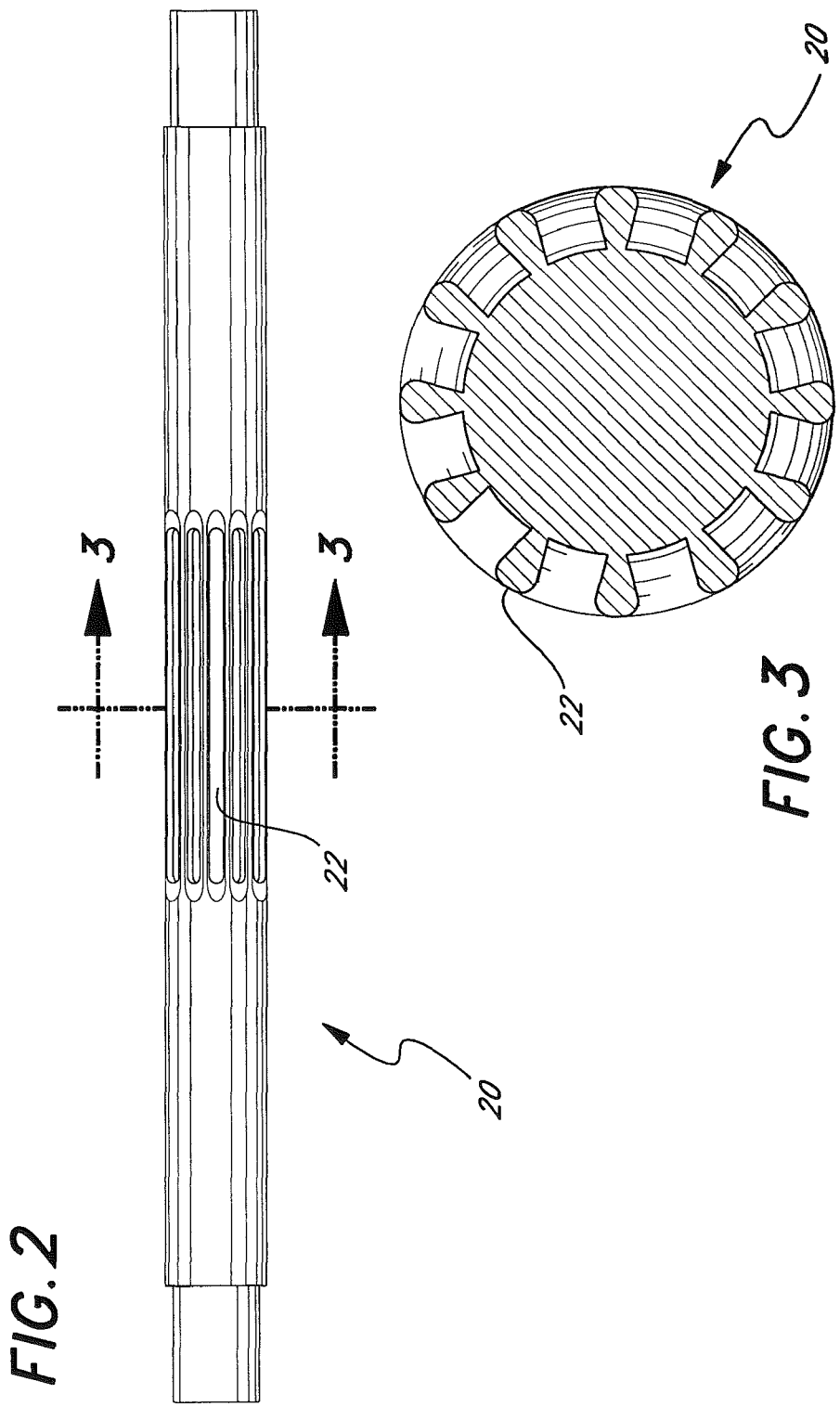

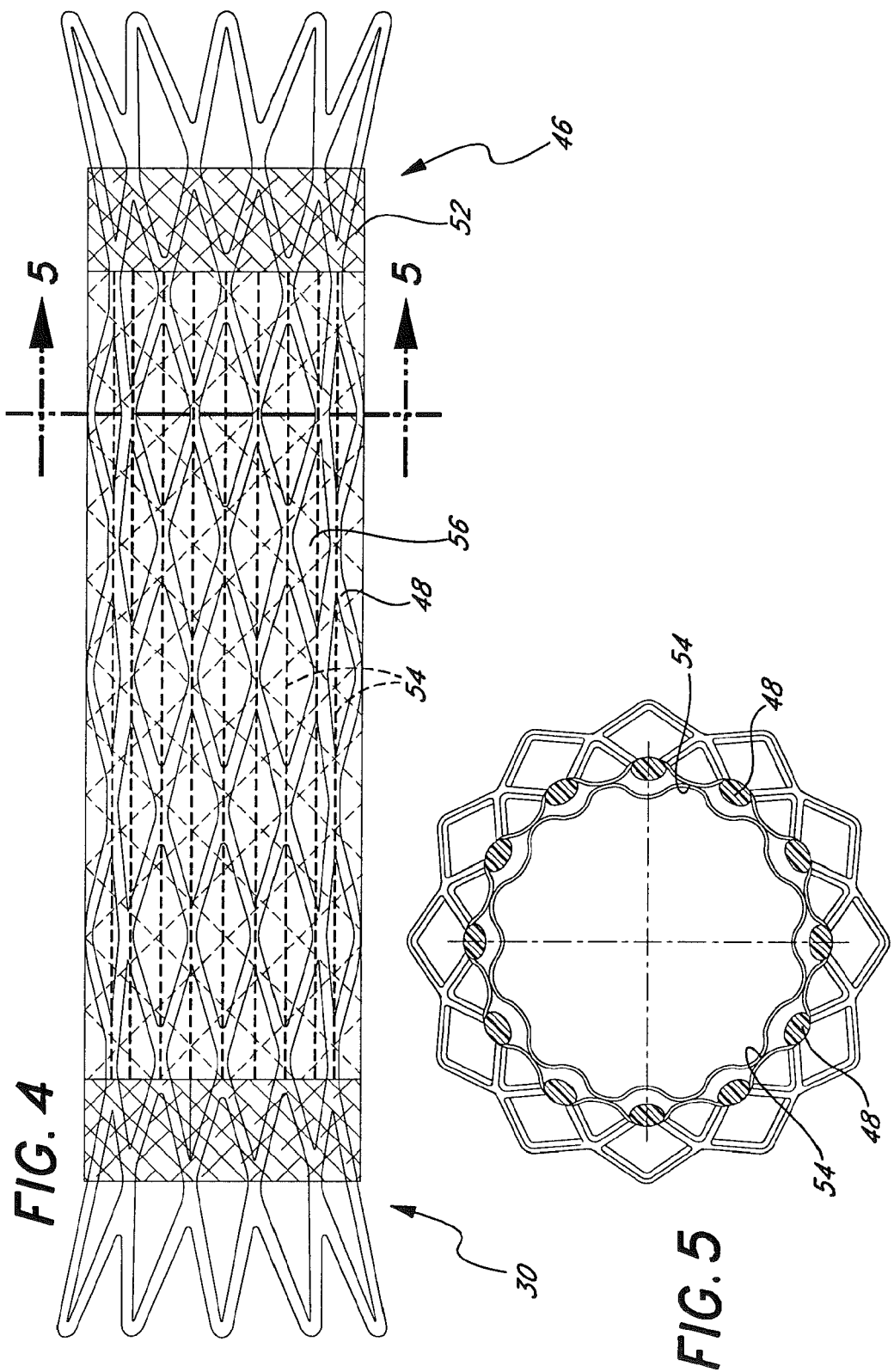

SELECTIVE ADHERENCE OF STENT-GRAFT COVERINGS

PRIORITY

This application is a continuation of U.S. application Ser. No. 13/225,028, filed Sep. 2, 2011, which is a continuation of U.S. application Ser. No. 11/363,689, filed Feb. 27, 2006, now U.S. Pat. No. 8,012,194, which is a continuation of U.S. application Ser. No. 10/410,589, filed Apr. 9, 2003, now U.S. Pat. No. 7,004,966, which is a continuation of U.S. application Ser. No. 09/764,811, filed Jan. 16, 2011, now U.S. Pat. No. 6,547,814, which is a division of U.S. application Ser. No. 09/409,209, filed Sep. 30, 1999, now U.S. Pat. No. 6,245,099, which claims the benefit under 35 U.S.C. § 119(e) to U.S. Provisional Application No. 60/102,518, filed Sep. 30, 1998, each of which is incorporated by reference into this application as if fully set forth herein.

BACKGROUND OF THE INVENTION

The use of implantable vascular grafts comprised of PTFE is well known in the art. These grafts are typically used to replace or repair damaged or occluded blood vessels within the body. However, if such grafts are radially expanded within a blood vessel, they will exhibit some subsequent retraction. Further, such grafts usually require additional means for anchoring the graft within the blood vessel, such as sutures, clamps, or similarly functioning elements. To minimize the retraction and eliminate the requirement for additional attachment means, those skilled in the art have used stents, such as those presented by Palmaz in U.S. Pat. No. 4,733,665 and Gianturco in U.S. Pat. No. 4,580,568, which are incorporated by reference into this application as if fully set forth herein, either alone or in combination with PTFE grafts.

For example, the stent described by Palmaz in U.S. Pat. No. 4,733,665 can be used to repair an occluded blood vessel. The stent is introduced into the blood vessel via a balloon catheter, which is then positioned at the occluded site of the blood vessel. The balloon is then expanded, thereby expanding the overlying stent to a diameter comparable to the diameter of an unoccluded blood vessel. The balloon catheter is then deflated and removed with the stent remaining seated within the blood vessel because the stent shows little or no radial retraction. Use of radially expandable stents in combination with a PTFE graft is disclosed in U.S. Pat. No. 5,078,726 to Kreamer, which teaches placing a pair of expandable stents within the interior ends of a prosthetic graft, having a length that is sufficient to span the damaged section of a blood vessel. The stems are then expanded to secure the graft to the blood vessel wall via a friction fit.

Although stents and stent/graft combinations have been used to provide endovascular prostheses that are capable of maintaining their fit against blood vessel walls, other desirable features are lacking. For instance, features such as increased strength and durability of the prosthesis, as well as an inert, smooth, biocompatible blood flow surface on the luminal surface of the prosthesis and an inert, smooth biocompatible surface on the abluminal surface of the prosthesis, are advantageous characteristics of an implantable vascular graft. Some skilled in the art have recently addressed these desirable characteristics by producing strengthened and reinforced prostheses composed entirely of biocompatible grafts and graft layers.

For example, U.S. Pat. No. 5,048,065, issued to Weldon, et al. discloses a reinforced graft assembly comprising a biologic or biosynthetic graft component having a porous surface and a biologic or biosynthetic reinforcing sleeve which is concentrically fitted over the graft component. The reinforcing sleeve includes an internal layer, an intermediate layer, and an external layer, all of which comprise biocompatible fibers. The sleeve component functions to provide compliant reinforcement to the graft component. Further, U.S. Pat. No. 5,163,951, issued to Pinchuk, et al. describes a composite vascular graft having an inner component, an intermediate component, and an outer component. The inner and outer components are preferably formed of expanded PTFE while the intermediate component is formed of strands of biocompatible synthetic material having a melting point lower than the material which comprises the inner and outer components.

Another reinforced vascular prosthesis having enhanced compatibility and compliance is disclosed in U.S. Pat. No. 5,354,329, issued to Whalen. This patent discloses a non-pyrogenic vascular prosthesis comprising a multilaminar tubular member having an interior stratum, a unitary medial stratum, and an exterior stratum. The medial stratum forms an exclusionary boundary between the interior and exterior strata. One embodiment of this prosthesis is formed entirely of silicone rubber that comprises different characteristics for the different strata contained within the graft.

The prior art also includes grafts having increased strength and durability, which have been reinforced with stent-like members. For example, U.S. Pat. No. 4,731,073, issued to Robinson, discloses an arterial graft prosthesis comprising a multi-layer graft having a helical reinforcement embedded within the wall of the graft. U.S. Pat. No. 4,969,896, issued to Shors describes an inner elastomeric biocompatible tube having a plurality of rib members spaced about the exterior surface of the inner tube, and a perforate flexible biocompatible wrap circumferentially disposed about, and attached to, the rib members.

Another example of a graft having reinforcing stent-like members is disclosed in U.S. Pat. No. 5,123,917, issued to Lee, which describes an expandable intraluminal vascular graft having an inner flexible cylindrical tube, an outer flexible cylindrical tube concentrically enclosing the inner tube, and a plurality of separate scaffold members positioned between the inner and outer tubes. Further, U.S. Pat. No. 5,282,860, issued to Matsuno et al. discloses a multi-layer stent comprising an outer resin tube having at least one flap to provide an anchoring means, an inner fluorine-based resin tube and a mechanical reinforcing layer positioned between the inner and outer tubes.

Still another stent-containing graft is described in U.S. Pat. No. 5,389,106 issued to Tower, which discloses an impermeable expandable intravascular stent including a dispensable frame and an impermeable deformable membrane interconnecting portions of the frame to form an impermeable exterior wall. The membrane comprises a synthetic non-latex, non-vinyl polymer while the frame is comprised of a fine platinum wire. The membrane is attached to the frame by placing the frame on a mandrel, dipping the frame and the mandrel into a polymer and organic solvent solution, withdrawing the frame and mandrel from the solution, drying the frame and mandrel, and removing the mandrel from the polymer-coated frame.

Microporous expanded polytetrafluoroethylene ("ePTFE") tubes may made by any of a number of well-known methods. Expanded PTFE is frequently produced by admixing particulate dry polytetrafluoroethylene resin with a liquid lubricant to form a viscous slurry. The mixture is poured into a mold, typically a cylindrical mold, and compressed to form a cylindrical billet. The billet is then ram extruded through an extrusion die into either tubular or sheet structures, termed extrudates in the art. The extrudates consist of extruded PTFE-lubricant mixture called "wet PTFE." Wet PTFE has a microstructure of coalesced, coherent PTFE resin particles in a highly crystalline state. Following extrusion, the wet PTFE is heated to a temperature below the flash point of the lubricant to volatilize a major fraction of the lubricant from the PTFE extrudate. The resulting PTFE extrudate without a major fraction of lubricant is known in the art as dried PTFE. The dried PTFE is then either uniaxially, biaxially or radially expanded using appropriate mechanical apparatus known in the art. Expansion is typically carried out at an elevated temperature, e.g., above room temperature but below 327° C., the crystalline melt point of PTFE. Uniaxial, biaxial or radial expansion of the dried PTFE causes the coalesced, coherent PTFE resin to form fibrils emanating from nodes (regions of coalesced PTFE), with the fibrils oriented parallel to the axis of expansion. Once expanded, the dried PTFE is referred to as expanded PTFE ("ePTFE") or microporous PTFE. The ePTFE is then transferred to an oven where it is sintered by being heated to a temperature above 327° C., the crystalline melt point of PTFE. During the sintering process the ePTFE is restrained against uniaxial, biaxial, or radial contraction. Sintering causes at least a portion of the crystalline PTFE to change from a crystalline state to an amorphous state. The conversion from a highly crystalline structure to one having an increased amorphous content locks the node and fibril microstructure, as well as its orientation relative to the axis of expansion, and provides a dimensionally stable tubular or sheet material upon cooling. Prior to the sintering step, the lubricant must be removed because the sintering temperature of PTFE is greater than the flash point of commercially available lubricants.

Sintered ePTFE articles exhibit significant resistance to further uniaxial, or radial expansion. This property has lead many in the art to devise techniques which entail endoluminal delivery and placement of an ePTFE graft having a desired fixed diameter, followed by endoluminal delivery and placement of an endoluminal prosthesis, such as a stent or other fixation device, to frictionally engage the endoluminal prosthesis within the lumen of the anatomical passageway. The Kreamer Patent, U.S. Pat. No. 5,078,726, discussed above, exemplifies such use of an ePTFE prosthetic graft. Similarly, International Publication Nos. WO95/05132 and WO95/05555, filed by W. L. Gore Associates, Inc., disclose balloon expandable prosthetic stents which have been covered on inner and outer surfaces by wrapping ePTFE sheet material about the balloon expandable prosthetic stent in its enlarged diameter, sintering the wrapped ePTFE sheet material to secure it about the stent, and crimping the assembly to a reduced diameter for endoluminal delivery. Once positioned endoluminally, the stent-graft combination is dilated to re-expand the stent to its enlarged diameter returning the ePTFE wrapping to its original diameter.

Thus, it is well known in the prior art to provide an ePTFE covering which is fabricated at the final desired endovascular diameter and is endoluminally delivered in a folded or crimped condition to reduce its delivery profile, then unfolded in vivo using either the spring tension of a self-expanding, thermally induced expanding structural support member or a balloon catheter. However, the known ePTFE covered endoluminal stents are often covered on only one surface of the stent, i.e., either the luminal and abluminal wall surfaces of the stent. Where the stent is fully covered on both the luminal and abluminal wall surfaces of the stent, the covering completely surrounds the stent elements and fills the stent interstices, thereby encapsulating the stent. Examples of patents teaching encapsulated stents and encapsulation techniques include commonly assigned patents: U.S. Pat. No. 5,749,880, U.S. Pat. No. 6,039,755, U.S. Pat. No. 6,124,523, and U.S. Pat. No. 6,451,047, each of which is incorporated into this application as if fully set forth herein.

When the encapsulated stent is comprised of shape memory alloy, characteristics of the stent make it necessary to encapsulate in the "large" state and then compress the encapsulated stent for delivery. In this case, encapsulation either increases the device's resistance to compression, or increases the delivery profile of the device as compression causes the polymeric material to fold or buckle around the stent. Perhaps the most serious problem is that the folding during compression actually encompasses folding of the stent itself, which unduly stresses the stent material and may result in structural failure.

In contrast to the prior art, the present invention provides a method to encapsulate a stent in ePTFE whereby the structure contains pockets or regions where the ePTFE layers are not adhered to one another allowing the stent to contractor or expand without being encumbered by ePTFE and without folding or stressing the stent itself.

As used herein, the following terms have the following meanings:

"Fibril" refers to a strand of PTFE material that originates from one or more nodes and terminates at one or more nodes.

"Node" refers to the solid region within an ePTFE material at which fibrils originate and converge.

"Internodal Distance" or "IND" refers to a distance between two adjacent nodes measured along the longitudinal axis of fibrils between the facing surfaces of the adjacent nodes. IND is usually expressed in micrometers (µm).

"Node Length" as used herein refers to a distance measured along a straight line between the furthermost end points of a single node which line is perpendicular to the fibrils emanating from the node.

"Nodal Elongation" as used herein refers to expansion of PTFE nodes in the ePTFE microstructure along the Node Length.

"Longitudinal Surface" of a node as used herein refers to a nodal surface from which fibrils emanate.

"Node Width" as used herein refers to a distance measured along a straight line, drawn parallel to the fibrils, between opposing longitudinal surfaces of a node.

"Plastic Deformation" as used herein refers to the deformation of the ePTFE microstructure under the influence of a expansive force which deforms and increases the Node Length and results in elastic recoil of the ePTFE material less than about 25%.

"Radially Expandable" as used herein to describe the present invention refers to a property of the ePTFE tubular member to undergo radially oriented Plastic Deformation mediated by Nodal Elongation.

"Structural Integrity" as used herein to describe the present invention in terms of the ePTFE refers to a condition of the ePTFE microstructure both pre- and post-radial deformation in which the fibrils are substantially free of fractures or breaks and the ePTFE material is free of gross failures; when used to describe the entire device "Structural Integrity" may also include delamination of the ePTFE layers.

Endoluminal stent devices are typically categorized into two primary types: balloon expandable and self-expanding. Of the self-expanding types of endoluminal stent devices, there are two principle sub-categories: elastically self-expanding and thermally self-expanding. The balloon expandable stents are typically made of a ductile material, such as stainless steel tube, which has been machined to form a pattern of openings separated by stent elements. Radial expansion is achieved by applying a radially outwardly directed force to the lumen of a balloon expandable stent and deforming the stent beyond its elastic limit from a smaller initial diameter to an enlarged final diameter. In this process the slots deform into "diamond shapes." Balloon expandable stents are typically radially and longitudinally rigid and have limited recoil after expansion. These stents have superior hoop strength against compressive forces but should this strength be overcome, the devices will deform and not recover.

Self-expanding stents, on the other hand, are fabricated from either spring metal or shape memory alloy wire which has been woven, wound or formed into a stent having interstices separated with wire stent elements. When compared to balloon-expandable stents, these devices have less hoop strength but their inherent resiliency allows them to recover once a compressive force that results in deformation is removed.

Covered endoluminal stents are known in the art. Heretofore, however, the stent covering has been made of a polymeric material which has completely subtended the stent interstices, that is, the stent was completely embedded in the polymeric material. This has posed difficulty particularly with the self-expanding stents. To preserve their self-expanding property, all covered self-expanding stents have been covered with a polymeric covering while the stent is in its unstrained dimensional condition (i.e., its native enlarged diameter). Yet in order to deliver a covered stent, it must be constricted to a smaller delivery diameter. Radial compression of a stent necessarily causes the individual stent elements to traverse the stent interstices and pass into proximity to a laterally adjacent individual stent element, thereby occupying the previously open interstitial space. Any polymeric material which subtends or resides within the previously open interstitial space will necessarily be displaced, either through shearing, fracturing or otherwise responding to the narrowing of the interstitial space as the stent is compressed from its enlarged unstrained diameter to its strained reduced diameter. Because the struts of the stent are completely encapsulated, resistance of the polymer may cause folding or stressing of the struts during compression.

It was recognized, therefore, that a need has developed to provide an encapsulating covering for a stent which is permanently retained on the stent, substantially isolates the stent material from the body tissue forming the anatomical passageway or from matter within the anatomical passageway, and which permits the stent to deform without substantial interference from the covering material.

It is, therefore, a primary objective of the present invention to provide a method for encapsulating an endoluminal stent such that the encapsulating covering forms non-adhered regions which act as slip planes or pockets to permit the individual stent elements to traverse a substantial surface area of interstitial space between adjacent stent elements without resistance or interference from the encapsulating covering, thereby avoiding damage or stress to the stent elements. It is a further object of the present invention to use the pockets between the bonded regions to contain and deliver therapeutic substances. It is another objective of the present invention to provide an apparatus for applying to and selectively adhering sections of the encapsulating covering about the stent, and to provide a selectively adhered encapsulated covered stent-graft device.

BRIEF SUMMARY OF THE INVENTION

Accordingly, the present invention relates generally to endoluminal stent-graft devices suitable for percutaneous delivery into a body through anatomical passageways to treat injured or diseased areas of the body. More particularly, the present invention relates to a method of bonding microporous polytetrafluoroethylene ("PTFE") coverings over a stent scaffold in a manner which maintains unbonded regions to act as slip planes or pockets to accommodate planar movement of stent elements. In one embodiment of the present invention bonded and unbonded regions are formed by means of a mandrel which has a pattern of either raised projections or recesses in its surface which are either synchronous or asynchronous, respectively, with stent elements.

In one embodiment, an encapsulated stent-graft device is provided in which an endoluminal stent having a plurality of individual stent elements separated by interstitial spaces is circumferentially covered along at least a portion of its longitudinal axis by at least one luminal and at least one abluminal covering of a polymeric material, the luminal and abluminal coverings being selectively adhered to one another at discrete portions thereof in a manner which forms a plurality of open pockets surrounding a plurality of stent elements. In another embodiment, a radially expandable reinforced vascular graft includes a first layer of biocompatible flexible material, a second layer of biocompatible flexible material, and a support layer sandwiched between the first and second layers of biocompatible flexible material.

In one embodiment, a selective bonding system can be advantageously used to produce inflatable pockets by bonding the first layer to the second layer in defined patterns. The resulting structure can then be inflated and stiffened by injection of a fluid resulting in a supporting structure without inclusion of a stent. A crude analogy might be the construction of an air mattress that is composed of flexible polymeric layers bonded to each other in a predetermined pattern.

The at least one luminal and at least one abluminal covering of a polymeric material are preferably comprised of expanded PTFE, unexpanded porous PTFE, woven polyester or expanded PTFE yarns, polyimides, silicones, polyurethane, fluoroethylpolypropylene (FEP), polypropylfluorinated amines (PFA), or other related fluorinated polymers. The stent may be made of any strong material which can undergo radial expansion but which is also resistant to non-elastic collapse such as silver, titanium, nickel-titanium alloys, stainless steel, gold, or any suitable plastic material capable of maintaining its shape and material properties at sintering temperatures and having the necessary strength and elasticity to enable radial expansion without collapse due to the presence of the polymer coverings.

A preferred embodiment of the radially expandable reinforced vascular device includes a tubular stent, having a plurality of stent elements and stent interstices, concentrically covered along at least a portion of its longitudinal length by a luminal polymeric covering and an abluminal polymeric covering. The luminal and abluminal polymeric coverings are discontinuously joined to one another through some of the stent interstices. The luminal and abluminal polymeric coverings may be shorter in length than the stent member to permit opposing stent ends to flare outwardly upon radial expansion of the stent member. Alternatively, the ends of the stent member may be completely encased by the luminal and abluminal polymeric coverings.

The stent member is preferably a self-expanding stent, which may be either an elastic spring material stent, such as a stainless steel stent as disclosed in U.S. Pat. No. 5,266,073 to Wall, a non-woven stainless steel self-expanding stent as disclosed in U.S. Pat. No. 5,282,824 to Gianturco, or a thermoelastic stent made of a shape memory alloy, e.g., a nickel-titanium alloy commonly known as NITINOL, such as that disclosed in U.S. Pat. No. 5,147,370 to McNamara et al., each of which is incorporated by reference into this application as if fully set forth herein. As used herein, a tubular shaped support member preferably comprises a stent made of silver, titanium, stainless steel, gold, or any suitable plastic material capable of maintaining its shape and material properties at sintering temperatures and having the strength and elasticity to permit radial expansion and resist radial collapse.

In accordance with the present invention, selective bonding of expanded PTFE luminal and abluminal layers encapsulates the endoluminal stent and isolates the stent from both the tissue forming the anatomical passageway as well as any fluid, such as blood, bile, urine, etc. which may pass through the anatomical passageway. The presence of slip planes or pockets formed by the selectively adhered regions of ePTFE: i) permits freedom of movement of stent elements within the encapsulating covering during both expansion and contraction of the stent along either its radial or longitudinal axes; ii) permits uniform folding of the ePTFE stent covering material which is complementary to the structure of the stent element lattice; iii) permits movement of the stent relative to the ePTFE encapsulating layers; iv) reduces forces required to compress or dilate the stent in the case of elastically or thermally self-expanding stents; v) reduces radial expansion pressings required to balloon expand an ePTFE encapsulated stent; and vi) provides void regions which may be used in conjunction with the microporous microstructure of the ePTFE covering material to retain and release bioactive substances, such as anticoagulant drugs, anti-inflammatory drugs, or the like.

Alternative arrangements of the stent member or other suitable structural support sufficient to maintain the lumenal patency of the lumenal and abluminal polymer coverings may be employed. For example, a radially expandable, articulated reinforced vascular graft may be formed by concentrically interdisposing a structural support assembly comprising multiple stent members spaced apart from one another between two tubular polymer covering members, then partially joining the two tubular polymer covering members by circumferentially compressing selected regions of the two tubular polymer covering members and thermally bonding the selectively compressed regions to one another.

The present invention also encompasses selective bonding of multiple polymeric layers to create an inflatable structure. Such a structure can be inflated by fluids delivered through lumens within the delivery catheter. The selective bonding method allows creation of devices with multiple adjacent channels or pockets. Some of these pockets can be pre-filled with a therapeutic drug to prevent restenosis or local thrombosis. Alternate pockets can be arranged for fluid inflation after the device is inserted.

One method of making the foregoing encapsulated stent-graft is to join concentrically a luminal polymeric tube, an endoluminal stent, and an abluminal polymeric tube and to place the assembly onto a mandrel having a plurality of raised projections separated by land areas, or by a plurality of land areas separated by a plurality of recesses. Either the raised projections or the land areas are patterned to match a pattern of either the stent elements of the stent interstices, both the stent elements and stent interstices or portions of each. In this way the projections or the landed areas exert pressure, respectively on select regions of the PTFE resulting in limited regions of adherence or fusion when the device is heated to sintering temperatures. Using a mandrel, luminal pressure is selectively applied to produce selectively placed bonds. As will become clear, bonding pressure can be applied from the luminal or the abluminal or both surfaces of the device.

The present invention is also directed to a process for making a radially expandable reinforced stent-graft device by: a) positioning a radially expandable stent member including a plurality of interconnected stent elements and a plurality of interstices between adjacent interconnected stent elements, concentrically over a first polymeric cover member; b) positioning a second polymer cover member concentrically over the radially expandable stent member and the first polymeric cover member; c) selectively joining portions of the first polymeric cover member and the second polymeric cover member through a plurality of the interstices of the stent member, while leaving portions of the first and second polymeric cover members unjoined and forming slip planes or pockets to accommodate movement of at least a portion of the interconnected stent elements therethrough; and d) fully joining opposing end regions of the first and second polymer cover members through the interstices of the stent member proximate to opposing ends of the stent member.

Fixing the support layer to the biocompatible graft layers includes selectively applying pressure to the portions of the luminal and abluminal polymer covers after they are loaded onto a mandrel and then heating the resulting assembly at sintering temperatures to form a mechanical bond at the selected areas of applied pressure. Alternatively, a pattern of at least one of an adhesive, an aqueous dispersion of polytetrafluoroethylene, a polytetrafluoroethylene tape, fluoroethylpolypropylene (FEP), or tetrafluoroethylene (collectively the "adhesive") may be introduced between the luminal and abluminal polymer covers at selected positions, followed by heating the assembly to the melt temperature of the adhesive to bond the luminal and abluminal polymer covers while leaving unbonded slip plane regions to accommodate movement of the stent elements. If ultraviolet curable adhesives are used, a UV laser or a photolithography system can be used to create the bond pattern. Many thermoplastic polymers such as polyethylene, polypropylene, polyurethane and polyethylene terephthalate can also be used. If pieces of one of these or similar polymers are placed or attached to one of the polymer covers in the region to be bonded, heat and pressure will melt the thermoplastic causing it to flow into the pores of the ePTFE, thereby bonding the ePTFE layers together.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 2 is a is a perspective view of a mandrel having longitudinal ridges or splines.

FIG. 3 is a is a cross-section view of the mandrel shown in FIG. 2.

FIG. 4 is a perspective view of a scent-graft device illustrating selected regions of bonding between the luminal and abluminal stent covers and a plurality of slip plane pockets intermediate the luminal and abluminal stent covers.

FIG. 5 is a is a cross-sectional view taken along line 5-5 of FIG. 4.

DETAILED DESCRIPTION OF THE PREFERRED EMBODIMENTS

Figure 1:
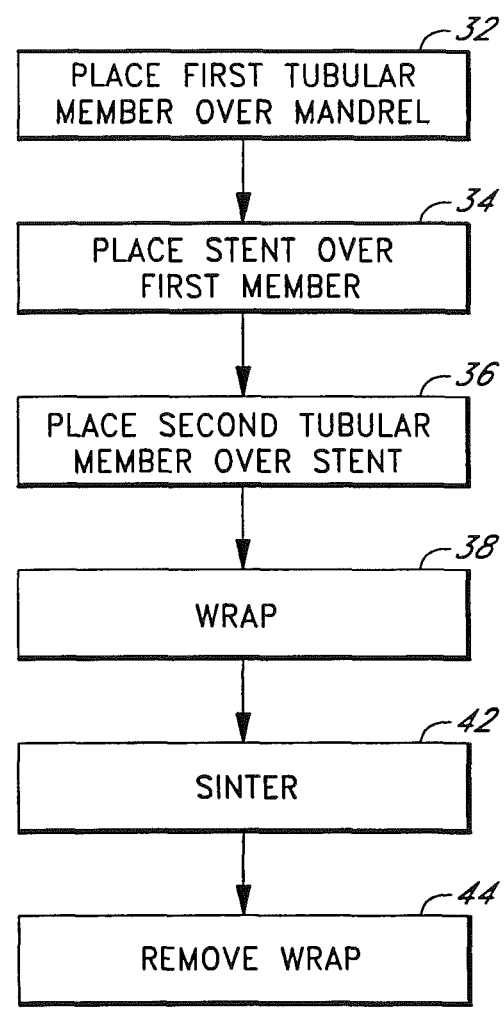
FIG. 1 is a is a process flow diagram illustrating a preferred method of making a stent-graft device.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The selective adherence encapsulation of the present invention is an improvement to the total adherence method taught in U.S. Pat. No. 5,749,880 that is incorporated by reference into this application as if fully set forth herein. The '880 patent discloses a method for encapsulating a support stent by placing the stent over a first tubular member of unsintered ePTFE and then placing a second tubular member of unsintered ePTFE coaxially over the stent so that the stent is sandwiched between two layers of ePTFE. Radial force is applied either internally or externally to force the first tubular member into contact with the stent and into contact with the second tubular members through openings in the stent or, respectively, to force the second tubular into contact with the stent and into contact with the first tubular member through openings in the stent. Finally, the compound structure is exposed to an elevated temperature to bond the first tubular member to the second tubular member wherever they are pressed into contact. In one embodiment an adhesive spread between the tubular members achieves the bonding. In a preferred embodiment the elevated temperature is a sintering temperature (above the crystalline melting point of PTFE) and direct PTFE to PTFE bonds form.

As mentioned above, a potential drawback of this approach is that when the radial dimensions of the stent change, movement of components of the stent (necessary for radial dimensional changes) may be impeded by surrounding ePTFE. If the stent is encapsulated in an expanded form and then reduced in diameter prior to insertion into a patient, the encapsulating ePTFE may significantly increase the force needed to compress the stent and may fold in a manner so as to increase the profile of the collapsed device. If the bonding of the first member to the second member is selective, i.e., does not occur through all available openings in the stent, slip planes or pockets will be left in the structure so that stent components can reorient within these pockets without encountering resistance from the ePTFE. Without the slip planes formed by the selective bonds of the present invention, crimping a shape memory stent may cause the stent members to fold or otherwise become stressed. This can result in permanent damage to the stent.

There is a considerable possible range of extent for the selective adherence of the instant invention. At one extreme a fully encapsulated stent as provided by the '880 patent in which there is full bonding between all areas of the two tubular members in which the stent struts do not block contact. At the other extreme would be a "spot welded" device where only tiny areas, probably in the middle of the open areas of the stent structure, are bonded. At that extreme, there might be a tendency for the PTFE members to separate from the stent should the spot weld bond strength be exceeded; however, the spot weld structure would provide virtually no impedance to radial deformation of the stent.

The optimum extent of selective adherence, as well as the geometric position of the bonds in relation to the stent, depends on the structure of the stent as well as the desired properties of the completed device. Complete control of the bond positions can be achieved by a numerically controlled (NC) machine in which the two-ePTFE members with the interposed stent are mounted on a mandrel that is attached to the spindle drive of a modified NC lathe. In this device a heated tool whose tip is equal to the desired spot weld area is automatically pressed onto the mandrel-mounted ePTFE-stent sandwich in proper registration to create a bond in an open region between components or struts of the stent. The tool moves away slightly as the mandrel turns to expose another open region and the tool then moves in to create a second bond and so on. Depending on the distance that the mandrel turns, the spot welds may be in adjacent open spaces or may skip one or more open spaces. As the mandrel is turned, the tool advances along the longitudinal axis of the mandrel so that virtually any patterns of spot welds can be created on the ePTFE-stent device. The precise pattern is under computer control and an entire stent can be treated quite quickly. If the design calls for spot welds of different surface areas, the stent can be treated with different tools (e.g., different areas) in several passes. An ultrasonic welding tip can readily be substituted for the heated tool. It is also possible to use radiant energy, as with a laser, to effect similar results. However, the inventors presently believe that pressure as well as heat are needed for the best bonds. Currently, laser-induced bonds do not appear to be as strong as bonds that are made with heat and pressure unless a curable adhesive system (as with a UV laser) is employed.

Splined or textured mandrels can also be used to apply selective heat and pressure to create selective adherence between the ePTFE members. By "spline or splined" is meant a cylindrical structure with longitudinally oriented ridges equally spaced about the structure's circumference. Wherever the first and second ePTFE tubular members come into contact a bond can be formed if heat and pressure are applied. If the ePTFE tubular members and support stent are placed over a mandrel whose surface is patterned with elevated and depressed regions (hills and valleys), the elevated regions or ridges will apply pressure to the overlying stent-ePTFE regions allowing selective bonding of those regions. Regions of ePTFE overlying valleys will not be pressed together and no bond will form there. That is, the pattern of the mandrel will be translated into an identical pattern of bonded regions in the stent-graft device. To make this translation, the process diagram of FIG. 1 is followed, as described below.

In a first step 32, a first ePTFE tubular member is placed on a mandrel. Preferably, the first tubular member is composed of unsintered ePTFE. In a second step 34, a stent device is placed over the first tubular member. In a third step 36, a second ePTFE tubular member is slid coaxially over the stent. The second tubular member may be unsintered or partially sintered. Use of a partially sintered second tubular member reduces the chance of tearing the member while pulling it over the stent. It will be apparent to one of skill in the art that there is an advantage to using a second tubular member with a slightly larger diameter than the first tubular member. However, if the second tubular member is too large, folds or creases may develop during the bonding process.

This entire process may use one of the textured mandrels that will be described below. However, it is also possible to assemble one or both tubular members and the stent on a smooth mandrel and then slip the assembly off the smooth mandrel and onto the textured mandrel. If the fit is fairly tight, it may be easier to place the stent over the first tubular member when that member is supported by a smooth mandrel. Also, there may be a limited number of textured mandrels available for production so that making a number of ePTFE-stent assemblies on less expensive smooth mandrels may result in a significant savings of time. If a smooth mandrel is used, the stent assembly is transferred to a textured mandrel before the next step (wrapping) occurs.

In a fourth step 38, the ePTFE-stent assembly is helically wrapped with PTFE "tape." This tape is actually a long, thin strip of PTFE of the type generally known as "plumbers tape." The tape is evenly wound over the stent device so that the device, is covered from end to end. The tape is wound so that the long axis of the tape is approximately normal (offset by 10-15°) to the long axis of the stent device. Ideally, there should be some overlap of the tape covering the device so that coverage is even and complete. In fact an overlap ratio wherein five revolutions is needed to progress one tape width has proven effective. The tape should be applied with a controlled and even tension so that it is sufficiently tight to apply pressure at right angles to the surface of the stent device. One way of achieving this is to use a force clutch on the tape spool to ensure a reproducible tension in the tape as it is wound over the stent device. While this process can be performed by hand, it is fairly easy to automate the winding process by having the mandrel mounted in a modified lathe. As the lathe spindle turns, the spool of tape automatically advances along the turning mandrel ensuring an even and reproducible wrapping.

In a fifth step 42, the wrapped assembly is then placed into an oven at a temperature above or nearly equal to the crystalline melting temperature of ePTFE. The wrapping applies pressure to regions of ePTFE that are underlaid by raised portions of the textured mandrel. The oven provides the necessary heat to cause a strong ePTFE-ePTFE bond to form in these regions. The sintering time can vary from a few minutes to a few tens of minutes. The overall time depends to some extent on the mass of the mandrel. If the mandrel is solid, it may take a considerable time for the surface of the mandrel to reach sintering temperatures. The process can be speeded up by using a hollow mandrel or even a mandrel containing a heating element so that the ePTFE is rapidly brought to a sintering temperature. A thermistor or similar temperature sensor is advantageous embedded into the surface of the mandrel so that it is possible to determine when the ePTFE reaches sintering temperature. In this way the process can be accurately timed.

In the final step 44, the tape is removed from the mandrel (after cooling) and the finished device is removed. Results in this step indicate the success of the sintering step 42. If sintering time or temperature is excessive, there may be some bonding of the PTFE tape to the stent device. The solution is to reduce the sintering time and/or temperature in future sintering. This is one reason that time, temperature and wrapping force should be carefully controlled. This problem can also be avoided by using means other than PTFE wrapping to apply pressure to the device during the sintering process. At first glance it would appear that the radial pressure can be applied by a "clam shell" heating device that clamps around the stent device and mandrel. However, such a device is not capable of applying even radial pressure. One possible solution is to divide the clam shell device into a number of segments, preferably at least six, each of which is equipped with pressure means to force the segment radially towards the center of textured mandrel. Similarly, the mandrel can be divided into segments or otherwise be capable of an increase in diameter (e.g., by formation from a material having a large coefficient of expansion upon temperature increase) to create radial pressure between the surface of the mandrel and the surrounding clam shell device.

An additional method of achieving bond pressure without wrapping is to use a clamshell device having an inner surface relief mirroring the textured mandrel. That is, there would be ridges and valleys that would exactly register with the ridges and valleys on the mandrel when the shell is closed. Similarly, a flat surface could be provided with ridges and valleys matching the mandrel surface if that surface were unrolled onto a flat plane. With such a surface it is possible to roll the mandrel in contact and registration with the flat pattern so that defined pressure is applied to the raised mandrel regions. The downward force applied to the mandrel controls the bond pressure while the rate of rolling controls the time a given bond is under pressure. This process can be carried out in an oven or the mandrel and surface can contain heating elements. One method of ensuring registration between the mandrel pattern and the flat surface pattern is to have gears attached to one or both ends of the mandrel mesh with a toothed rack that runs along one or both edges of the patterned surface. Contact pressure is controlled by weight of the mandrel or by a mechanical linkage that applies a controlled downward force to the mandrel.

To this point no mandrel patterns or textures have been described. It will be clear to one skilled in the art that this invention permits a complex pattern wherein the entire stent structure is mirrored by the valleys and ridges of the mandrel with the structural members of the stent fitting into the valleys and the apices of the ridges or raised portions falling at discrete points within the open areas of the stent. What may be somewhat less obvious is that far simpler patterns can also produce excellent results in the present invention. One simple mandrel design is a "splined" mandrel wherein the mandrel has a number of longitudinal ridges (splines) so that a cross-section of the mandrel looks something like a toothed gear. FIG. 2 shows a perspective view of such a mandrel 20 with longitudinal splines 22. FIG. 3 shows a cross section of the mandrel 20 wherein it is apparent that the splines 22 have rounded edges to avoid damaging or cutting the surface of the ePTFE.

Figure 6:
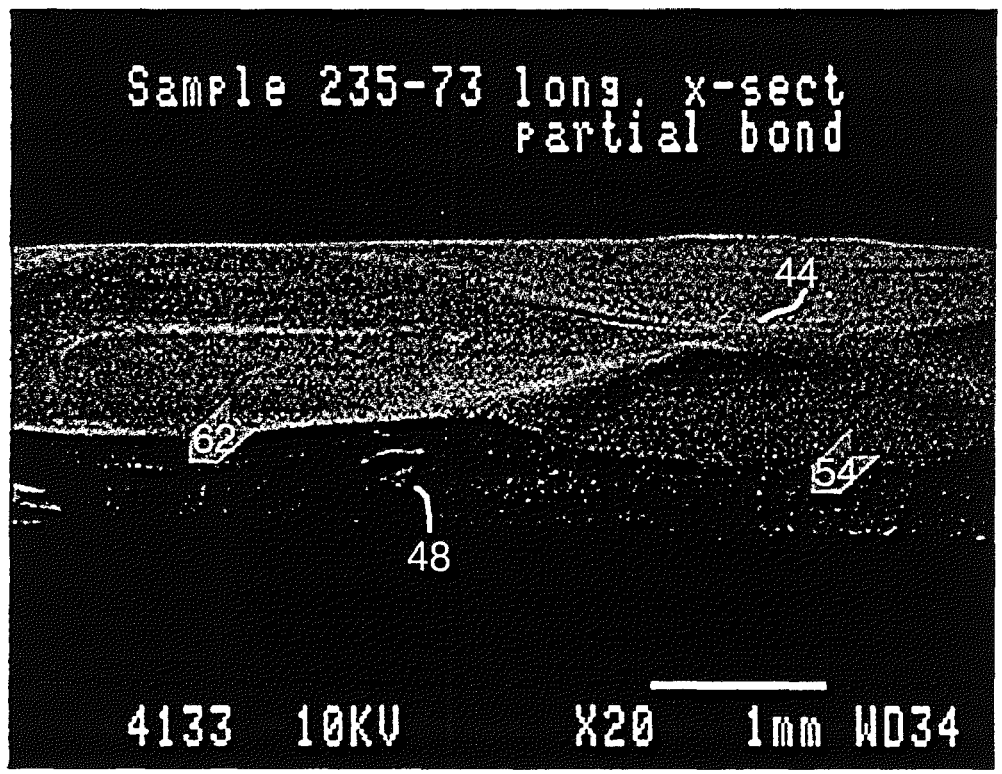
FIG. 6 is a scanning electron micrograph illustrating a selectively bonded region and a slip plane pocket with a stent element residing therein.

FIG. 4 shows a perspective view of an encapsulated stent 30 made on the splined mandrel 20. The stent 46 is composed of struts 48 arranged in a diamond pattern. Regions 52 at the ends of the device (marked by cross-hatching) have complete bonding between the two-ePTFE tubular members. This region is produced by smooth, non-splined regions of the mandrel. Dotted lines 54 mark the position of the splines and the resulting regions of selective bonding. That is, the device has spaced apart bonded regions running the length of the open diamond regions 56. Because of this orientation, successive tiers of diamond regions 56 along the longitudinal axis of the device are alternately bonded and unbonded. FIG. 6 shows a scanning electron micrograph of an oblique section through a longitudinally selectively bonded stent 44. A cross-section of the strut 48 is shown as well as a bonded region 54 and an unbonded slip pocket 62. The unbonded pockets 62 allow free movement of the stent struts 48. However, even those diamond regions 56 containing bonds 54 allow relatively unimpeded movement of the struts 48 because the bond 54 is only down the central part of the diamond region 56—relatively distant from the struts 48. Tests show that the selectively bonded stent 30 can be radially compressed with considerably less force than a stent that is encapsulated by uniformly bonding all regions where the ePTFE tubular members contact each other. The longitudinal bonds somewhat restrict longitudinal compression of the device as the bonded regions buckle less readily than unbonded ePTFE.

Figure 7:
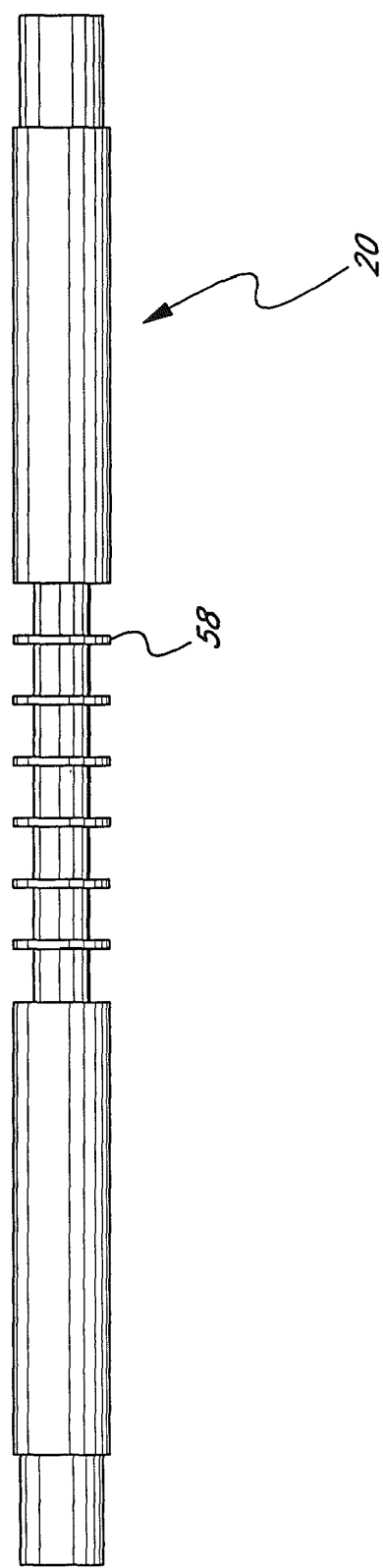
FIG. 7 is a is a perspective view of a mandrel having circumferential ridges (as opposed to longitudinal splines).

The longitudinal bonds 54 do restrict the side to side flexibility or bendability of the device to some extent. In some applications this stiffening of the device is desirable while in other applications one needs a stent device that is able to bend more freely. Increased lateral flexibility can be achieved by using a mandrel with radial ridges rather than longitudinal ridges as shown in FIG. 7. Again the ridges 58 are spaced apart in relation to the strut 48 spacing in the stent to be encapsulated. If the stent 46 shown in FIG. 4 is used, the radial ridges 58 can be spaced apart to place circumferential bonds through alternate tiers of diamond regions 56. The resulting device is more bendable laterally than the version with longitudinal bonds. In addition, the circumferential bonds result in a device that is more easily compressed longitudinally.

It is clear that the area and orientation of the bond regions influence the properties of the final device. For example, a helical pattern of ridges produces a device with intermediate properties: it is more laterally bendable that the longitudinally bonded device of FIG. 4, but it has more resistance to longitudinal compression than does a device with circumferential bonds. The pitch of the helical pattern controls the overall effect with shallow pitches acting more like circumferential ridges and steep pitches acting more like longitudinal ridges. Multiple helices can be used with opposing (e.g., clockwise and counter clockwise) ridges, producing a device that is more resistant to lateral bending. Virtually any combination of the described patterns can be used to produce devices having a preferred direction of bendability or devices that resist longitudinal compression in one region while permitting such compression in another.

The stent device illustrated in the figures is one in which the stent struts form courses or diamond-shaped spaces and the struts continue from course to course to create an extended tubular device. Stents are also available which consist of only a single course (or segment) of diamond-shapes. The current method can advantageously be used to combine a number of these segments together to make an extended tubular device. Frequently, these single segment stents consist of an alternation of larger and smaller diamond shapes. For example, the segments can be arranged with large diamonds touching large diamonds. Other arrangements included a "twisted" design wherein each successive segment is rotationally offset and an "alternating" design wherein alternate segment are rotated so that a given large diamond is bounded on either side by a small diamond. The precise properties of the resulting encapsulated device depend on these factors. However, the significant thing about the prior art encapsulation is that it produced a device that is relatively stiff and unbending.

Figure 8:
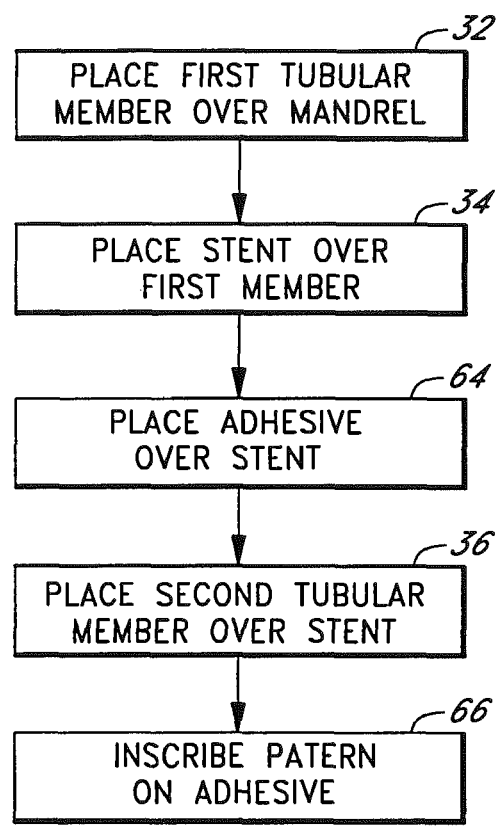
FIG. 8 is a is a flow diagram showing a method of using adhesives to create selective adherence.

Various adhesives (as opposed to directly adhering PTFE to PTFE) can also be used to create the pattern of bonded regions. FIG. 8 shows a diagram of one method for using adhesives to create selective bonds. In a first step 32, a tubular graft member is placed on a support such as a mandrel. In a second step 34, a stent (or stents) is placed over the first graft member. In a third step 64, a coating of adhesive is placed over the stent graft combination. This adhesive is one that is "activatable" meaning that the material is not inherently sticky as it is applied. However, it can be activated by applying heat, light or some other energy so that it hardens or otherwise changes to form a permanent bond. In the next step 64, a second tubular member is placed over the adhesive-coated stent. In the final step 66, a pattern of desired bonds is inscribed on the device with, for example, a laser or a heated probe or a photolithographic mask image. The inscribing process provides energy to local regions of the structure to activate the adhesive and create selectively bonded regions. A number of different activatable adhesive materials can be used in the present invention. One such material might be a layer or coating of a thermoplastic such as polyethylene. This material can be activated by heat that melts it so that it flows into the pores of the ePTFE. After cooling, the plastic hardens so that the PTFE of one tubular member is bonded to the other tubular member.

Figure 9:
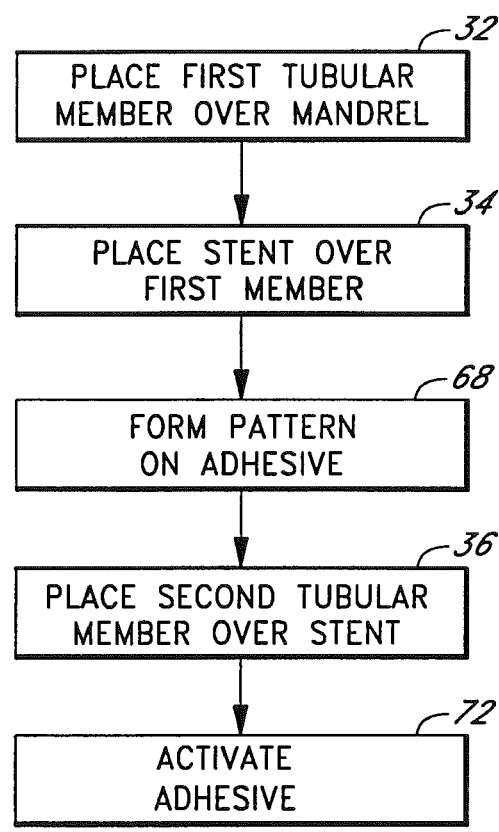
FIG. 9 is a flow diagram of an alternative method of using adhesives to creates selective bonds.

FIG. 9 shows a second adhesive-based method of creating selective bonds. The initial steps are the same as in the previous method. However, in step 68 the adhesive material is applied selectively to form the future pattern. This can be done, for example, by a screening or offset printing method. An inherently sticky adhesive can be used or an activatable adhesive (as in the previous method) can be employed. The second tubular member is applied (step 36) and the adhesive pattern is formed either by applying pressure (when using an inherently sticky adhesive) or by applying pressure followed by an activate adhesive step 72 (for example, heating to melt a thermoplastic adhesive).

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method for making a radially expandable stent-graft comprising forming an assembly by
    positioning a first polymeric member over a smooth surface;
    and
    positioning a stent comprising elements concentrically over the first polymeric member, wherein the stent has a plurality of openings;
removing the assembly from the smooth surface and positioning the assembly onto a surface having a pattern of elevated regions before covering at least part of the assembly by positioning a second polymeric member over the assembly;
applying pressure to force the first polymeric member and the second polymeric member into intimate contact through the openings in the stent at selective locations to form slip planes between the first and second polymeric members to accommodate movement of at least some of the stent elements; and
joining the first and second polymeric members to form a pattern of bonds at the locations.

2. The method of claim 1 wherein the elevated regions coincide with the locations.

3. The method according to claim 2 wherein the joining step includes inserting the stent-graft into a heating device having an inner surface that mirrors the pattern of elevated regions and registers with the locations when the heating device is closed.

4. The method according to claim 2 wherein the step of positioning a stent further comprises applying an activatable adhesive coating to the stent and first polymeric member.

5. The method according to claim 4 wherein the joining step comprises an inscribing process that provides energy to the selective locations to activate the adhesive.

6. The method according to claim 5 wherein the activatable adhesive is applied in a pattern to enable joining at the locations.

* * * * *